United States Patent
Kaneko et al.

(10) Patent No.: US 6,830,896 B2
(45) Date of Patent: Dec. 14, 2004

(54) PROCESS FOR ANALYZING ANNEXIN-V IN URINE, AND APPLICATION THEREOF

(75) Inventors: Noboru Kaneko, 23-12-403, Kasuga 2-chome, Bunkyo-ku, Tokyo 112-0003 (JP); Ryuko Matsuda, Annex 202 to Runeprattsu, 1-25, Midori-cho 4-chome, Mibu-machi, Shimotsuga-gun, Tochigi 321-0204 (JP); Tadahiro Kajita, Hyogo-ken (JP)

(73) Assignees: Noboru Kaneko, Tokyo (JP); Ryuko Matsuda, Tokyo (JP)

(*) Notice: Subject to any disclaimer, the term of this patent is extended or adjusted under 35 U.S.C. 154(b) by 0 days.

(21) Appl. No.: 10/294,558

(22) Filed: Nov. 15, 2002

(65) Prior Publication Data

US 2003/0124637 A1 Jul. 3, 2003

Related U.S. Application Data

(62) Division of application No. 09/319,448, filed as application No. PCT/JP98/04552 on Oct. 8, 1998, now abandoned.

(30) Foreign Application Priority Data

Oct. 8, 1997 (JP) ............................................. 9-312573

(51) Int. Cl.$^7$ .................... G01N 33/543; G01N 33/577; C07K 16/28
(52) U.S. Cl. ...................... 435/7.94; 435/7.1; 435/7.21; 435/7.92; 435/70.21; 435/332; 435/334; 435/337; 436/518; 436/548; 436/811; 530/388.2; 530/388.22; 530/388.25; 530/389.1; 530/389.3; 530/391.1
(58) Field of Search ................................ 435/7.1, 7.21, 435/7.92, 7.94, 70.21, 332, 334, 337, 975; 436/518, 548, 811; 530/388.2, 388.22, 388.25, 389.1, 389.3, 391.1

(56) References Cited

U.S. PATENT DOCUMENTS 5,632,986 A * 5/1997 Tait et al. ................ 424/94.64
5,767,247 A * 6/1998 Kaneko et al. ............ 530/388.2

FOREIGN PATENT DOCUMENTS

WO 96/15152 * 5/1996

OTHER PUBLICATIONS

Nakao et al., 1990. An enzyme–linked immunosorbent assay system for quantitative determination of calphobindin I, a new placental anticoagulant protein, and its application to various specimens. Chem. Pharm. Bull. 38(7): 1957–60.*
Nakao et al., 1994. A new function of calphobindin I (annexin V). Promotion of both migration and urokinase–type plasminogen activator activity of normal human keratinocytes. Eur. J. Biochem. 223: 901–908.*
Kaneko et al., 1996. Measurement of plasma annexin V by ELISA in the early detection of acute myocardial infarction. Clinica Chimica Acta 251: 65–80.*

* cited by examiner

Primary Examiner—Christopher L. Chin
Assistant Examiner—James L. Grun
(74) Attorney, Agent, or Firm—Sughrue Mion, PLLC

(57) ABSTRACT

The present invention provides a process and regent for analyzing annexin-V, wherein the measurement of a concentration of annexin-V can be easily carried out without need for addition of chemicals for inhibiting the bonding of various proteins with calcium ion and for adjusting a specimen solution to the specimen at a measuring stage, and a process and medicine for diagnosing an internal organ disorder based on the analyzing process and regent. A urine is brought into contact with an anti-annexin-V monoclonal antibody to perform an antigen-antibody reaction of annexin-V in the urine with the anti-annexin-V monoclonal antibody, thereby forming an annexin-V antigen/anti-annexin-V monoclonal antibody complex, and the amount of the formed annexin-V antigen/anti-annexin-V monoclonal antibody complex is quantitatively measured. Thus, it is possible to carry out the measurement of the concentration of annexin-V in the urine, and it is possible to carry out the diagnosis of an internal organ disorder such as a disseminated intravascular coagulation syndrome, the diagnose of acute nephritis and the like by a analyzed value of concentration of annexin-V measured in the urine.

5 Claims, 2 Drawing Sheets

CONCENTRATION OF HUMAN-ANNEXIN-V (ng/ml)

PROCESS FOR ANALYZING ANNEXIN-V IN URINE, AND APPLICATION THEREOF

This is a divisional of application Ser. No. 09/319,448 filed Sep. 10, 1999, now abandoned, which is a 371 of PCT/JP98/04552, filed Oct. 8, 1998 the disclosure of which is incorporated herein by reference.

FIELD OF THE INVENTION

The present invention relates to a process for qualitatively and quantitatively analyzing a protein annexin-V which is present in a urine of a human and a mammalian animal (and which will-be referred to as annexin-V in a urine hereinafter), as well as a qualitatively and quantitatively analyzing regent and an application thereof.

The present invention also relates to a process for quantitatively analyzing annexin-V present in a urine using anti-annexin-V monoclonal antibody and polyclonal antibody having a specificity to an antigenic determinant side on a protein of a protein annexin-V, present in a human and a mammalian animal, thereby detecting the presence and absence of an organopathy of an internal organ such as kidney, heart and lung, which is combined with, for example, a disseminated intravascular coagulation syndrome (DIC) or a septicemia of a human by the resulting content of annexin-V in the urine, whereby particularly the disseminated intravascular coagulation syndrome (DIC) can be early diagnosed, and a diagnosis medicine for use in such analyzing process.

Further, the present invention relates to the measurement of annexin-V present in a urine of a human and a mammal such as a rat, which is capable of diagnosing the presence or absence of an organopathy of an internal organ by experimentally measuring a concentration of annexin-V in a urine of a rat, for example, measuring a concentration of annexin-V in a urine at the time when the blood annexin-V concentration has been risen, as well as the application or utilization thereof for the therapy of disseminated intravascular coagulation syndrome and for the development of an effective therapeutic medicine.

Yet further, the present invention relates to a process for quantitatively analyzing annexin-V present in a urine of a human and a mammal using an anti-annexin-V monoclonal antibody and polyclonal antibody having a specificity to antigenic determinant sides on a protein of a protein annexin-V in the human and the mammal, thereby enabling the diagnosis, particularly, of myocardial infarction and angina pectoris, based on the content of the annexin-V in the urine, and to a diagnosis medicine for use in such diagnosis.

BACKGROUND ART

The detection of the presence or absence of a disease of an internal organ with a substance present in a urine is less often than with a substance in blood or serum. The reason is that each of various substances in the urine and the value of pH of the urine exert an influence to a system to be measured.

As used in the present invention, the annexin-V which is an antigen is a protein having a molecular weight, for example, of 32 to 35 K dalton, i.e., a calcium-binding protein present in tissues and cells of a human and various mammals. The annexin-V is present in a soluble component of a cytoplasm and forms a family by an amino acid sequence. Presently, annexin I to XII are known. It is also known that the annexin can be bonded with phosphatide or actin depending on the concentration of calcium to exhibit anti-inflammatory effect and an anti-coagulation effect.

It has been reported that an annexin, which is one member of an annexin family, is contained in the lung, heart and kidney in the content increased in the named order, and is contained in a smaller content in the cerebrum and liver (see Heart Vessels, 1994, 9: 148–154). The present inventors have reported that the measurement of a concentration of annexin-V in blood is effective, for example, for the diagnosis of myocardial infarction, when the necrosis of tissues and cells has occurred, from the viewpoint that the annexin-V early departs into the blood (see Literature CCA, 1996), and has proposed a process for analyzing annexin-V present in blood using an anti-annexin-V antibody (see International Publication Number: WO96/15152 internationally published in May 23, 1996).

However, the measurement of a concentration of annexin-V in blood suffers from a problem that a pain is inflicted to a subject upon the drawing blood, and the concentration of annexin-V must be measured within a short period of time after the drawing blood, but much labor is required to separate serum from the drawn blood. Another problem is that EDTA must be added in order to control the bonding of various proteins contained in serum with calcium ion, and much labor is required for the preparation and addition of such a solution.

DISCLOSURE OF THE INVENTION

It is less often to detect the presence or absence of an organopathy of an internal organ with a substance present in a urine, than in a blood or serum, because a system to be measured is largely influenced by each of various substances contained in a urine and a larger value of pH of the urine. However, the present inventors have found from the subsequent researches and studies that the annexin-V in the urine stoichiometrically forms an antigen/antibody complex in a urine by an antigen-antibody reaction with an anti-annexin-V monoclonal antibody.

Further, the present inventors have found that the protein annexin-V in a human and a mammal is usually present only in an amount of about 2 ng/ml in a urine in a healthy person, but when a person has an organopathy in an internal organ, wherein the content of annexin-V departing from the internal organ is larger, the annexin-V appearing in his or her blood also appears immediately in his urine.

Yet further, from the viewpoint that if a concentration of annexin-V appearing in a urine can be measured quantitatively, the presence or absence of an organopathy can be diagnosed, the present inventors have found by continuing the measurement of the concentration of annexin-V in the urine that when it is observed, by continuing the measurement of the concentration of annexin-V in the urine, that the rising of the concentration of annexin-V in the urine has occurred, for example, due to an internal organ disorder or the destruction of tissues of kidney caused by a blood circulation failure in a capillary vessel, the amount of annexin-V in the urine is increased, and that the degree of a disorder of an internal organ such as lung, heart and kidney and the therapy and recuperation of such disorder can be diagnosed early, based on an increase or decrease in concentration of the annexin-V in the urine. Moreover, the present inventors have found that the rising of the concentration of annexin-V is observed in a urine in acute nephritis, but not observed in blood.

It is an object of the present invention to provide a process for analyzing annexin-V, wherein the measurement of annexin-V can be carried out easily without need for the addition of a regent for inhibiting the bonding of various proteins with calcium ion and for regulating a specimen solution, and a process for diagnosing an internal organ disorder or the like, based on such analyzing process.

The present invention resides in a process for analyzing annexin-V in a urine, comprising steps of bringing a urine into contact with an anti-annexin-V monoclonal antibody to perform an antigen-antibody reaction of annexin-V present in the urine with the anti-annexin-V monoclonal antibody, thereby forming an annexin-V antigen/anti-annexin-V monoclonal antibody complex, and quantitatively measuring the amount of the formed annexin-V antigen/anti-annexin-V monoclonal antibody complex. The present invention also resides in a process for analyzing annexin-V in a urine, comprising the steps of bringing a urine into contact with a first anti-annexin-V monoclonal antibody fixed in a solid phase to perform an antigen-antibody reaction of annexin-V present in the urine with the first anti-annexin-V monoclonal antibody, thereby forming an annexin-V antigen/first anti-annexin-V monoclonal antibody complex; bonding an anti-dog-annexin-V polyclonal labeled antibody or a second anti-annexin-V monoclonal labeled antibody to the annexin-V antigen of the formed antibody complex to form a bonded antibody complex/anti-annexin-V polyclonal or second anti-annexin-V monoclonal labeled antibody product; and quantitatively measuring the amount of the formed labeled antibody bonded product. Further, the present invention resides in a regent for analyzing annexin-V in a urine, comprising a first anti-human-annexin-V monoclonal antibody having a specificity to an antigen determinant site on the protein of a human annexin-V antigen fixed in a solid phase, and a second anti-human-annexin-V monoclonal labeled antibody or an anti-dog-annexin-V polyclonal labeled antibody having a binding specificity to the antigen determinant site on the protein of the human annexin-V antigen.

In addition, the present invention is directed to a process for diagnosing an organopathy, comprising the steps of measuring a concentration of annexin-V in a urine, and comparing the measured value of the concentration of the annexin-V in the urine with a normal value of concentration of annexin-V. Further, the present invention is directed to a process for diagnosing an organopathy by use of a urine, comprising the steps of bringing a urine into contact with a first anti-annexin-V monoclonal antibody to perform an antigen/antibody reaction of annexin-V in the urine with the first anti-annexin-V monoclonal antibody, thereby forming an annexin-V antibody/first anti-annexin-V monoclonal antibody complex; bonding an anti-dog-annexin-V polyclonal labeled antibody or a second anti-annexin-V monoclonal labeled antibody to the annexin-V antigen of the formed antibody complex to form a bonded product of anti-dog-annexin-V polyclonal labeled antibody or second anti-annexin-V monoclonal labeled antibody/annexin-V antigen/antibody complex; and quantitatively measuring the amount of the formed bonded product of anti-dog-annexin-V polyclonal labeled antibody or second anti-annexin-V monoclonal labeled antibody/annexin-V antigen/antibody complex. Yet further, the present invention is directed to a medicine for diagnosing an organopathy by using a urine as specimen, comprising a first anti-human-annexin-V monoclonal antibody having a binding specificity to an antigen determinant site on the protein of a human annexin-V antigen fixed in a solid phase, and a second anti-human-annexin-V monoclonal labeled antibody or an anti-dog-annexin-V polyclonal labeled antibody having a binding specificity to the antigen determinant site on the protein of the human annexin-V antigen.

Yet further, the present invention is directed to a process for diagnosing acute nephritis by use of a urine, comprising the steps of bringing samples of urine taken at two different time points into contact with an anti-annexin-V monoclonal antibody to perform an antigen/antibody reaction of annexin-V in each of the urine samples with the anti-annexin-V monoclonal antibody, thereby forming an annexin-V antigen/anti-annexin-V monoclonal antibody complex; quantitatively measuring the amount of the formed annexin-V antigen/anti-annexin-V monoclonal antibody complex, thereby determining a concentration of annexin-V in each of the urine samples to determine a difference between the concentrations of annexin-V in the urine samples taken at the two different time points from the values of the concentrations of annexin-V in the urine samples taken at the two different time points; and on the other hand, bringing annexin-V present in a specimen derived from samples of blood drawn at the two different time points into an antigen/antibody reaction with an anti-annexin-V monoclonal antibody to form an annexin-V antigen/anti-annexin-V monoclonal antibody complex; quantitatively measuring the amount of the formed annexin-V antigen/anti-annexin-V monoclonal antibody complex, thereby determining a concentration of annexin-V in each of the blood samples to determine a difference between the concentrations of annexin-V in the blood samples drawn at the two different time points; and comparing the differences between the annexin-V concentrations in the urine samples and the blood samples taken at the two different time points with each other. Additionally, the present invention is directed to a process for diagnosing acute nephritis by use of a urine, comprising the steps of bringing samples of urine taken at two different time points into contact with an anti-annexin-V monoclonal antibody to perform an antigen/antibody reaction of annexin-V in each of the urine samples with the anti-annexin-V monoclonal antibody, thereby forming an annexin-V antibody/anti-annexin-V monoclonal antibody complex; quantitatively measuring the amount of the formed annexin-V antibody/anti-annexin-V monoclonal antibody complex, thereby determining a concentration of annexin-V in each of the urine samples to determine a difference between the concentrations of annexin-V in the urine samples taken at the two different time points from the values of the concentrations of annexin-V in the urine samples at the two different time points; and on the other hand, bringing annexin-V in a specimen derived from samples of blood drawn at the two different time points into an antigen/antibody reaction with an anti-annexin-V monoclonal antibody, thereby forming an annexin-V antigen/anti-annexin-V monoclonal antibody complex; quantitatively measuring the amount of the formed annexin-V antigen/anti-annexin-V monoclonal antibody complex, thereby determining a concentration of annexin-V in each of the blood samples to determine a difference between the concentrations of annexin-V in the blood samples at the two different time points; and comparing the differences between the concentrations of annexin-V in the urine samples and the blood samples taken at the two different time points with each other. Further, the present invention is directed to a medicine for diagnosing acute nephritis by use of a urine, comprising a regent for analyzing annexin-V present in a urine, and a regent for analyzing annexin-V present in blood.

BRIEF DESCRIPTION OF THE DRAWINGS

A mode for carrying out the present invention will now be described by way of examples with reference to the accompanying drawings, wherein the present invention is not limited in any way to the following illustration and description.

In FIG. 1, the axis of ordinate indicates the difference absorbance obtained by subtracting an absorbance measurement at the secondary wavelength of 690 nm from an absorbance measurement at the primary wavelength of 492 nm, and the axis of abscissa indicates the concentration of native human annex-V, wherein each of ○ marks represents the average value of the difference absorbances measured four times, and the length of a line extending upwards and downwards from each of the ○ marks represents an average value ±2SD.

In FIG. 2, the axis of ordinate indicates the difference absorbance obtained by subtracting an absorbance measurement at the secondary wavelength of 690 nm from an absorbance measurement at the primary wavelength of 492 nm, and the axis of abscissa indicates the concentration of native human annex-V, wherein each of □ marks represents the average value of the difference absorbances measured four times, and the length of a line extending upwards and downwards from each of the □ marks represents an average value ±2 SD.

BEST MODE FOR CARRYING OUT THE INVENTION

Figure 1:
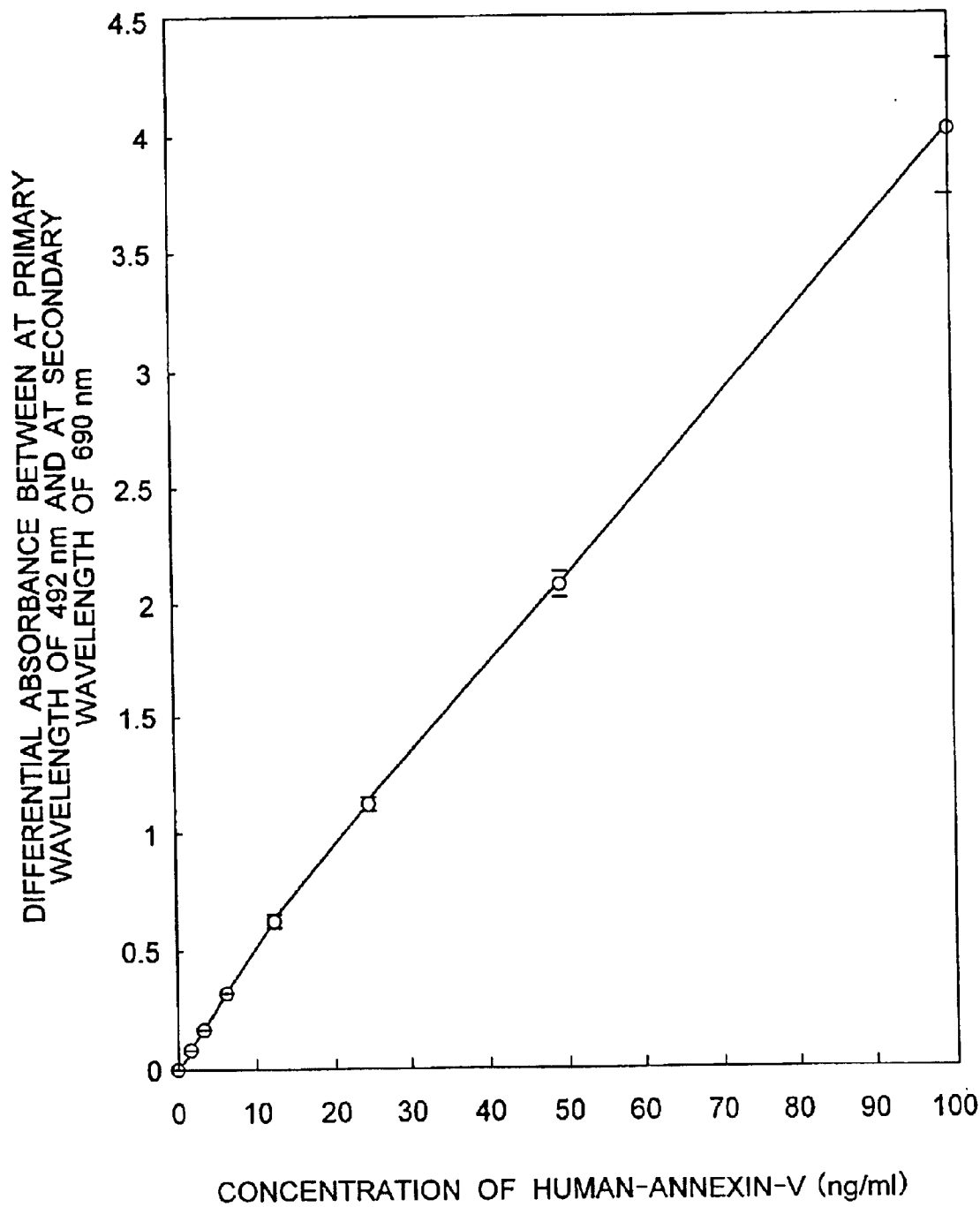
FIG. 1 is a calibration graph which is used in one embodiment for measuring a concentration of human annexin-V in a urine according to the present invention, and which is used in the measurement of a concentration of human annexin-V in a urine by ELISA process using a combination of an HRPO-labeled antibody derived from an anti-annexin-V monoclonal antibody produced by an anti-annexin-V monoclonal antibody-producing hybridoma cell line clone HDA-907 of the accession number FERM BP-5286 deposited in the International Depositary Authority for the deposit of microorganism (Life Engineering Industrial Technology Research Institute belonging to Industrial Technology Board in Ministry of International Trade and Industry, 1–3, Higasi 1-Choume, Tsukuba-shi, Ibaragi-ken, Japan), and a solid phase anti-human-annexin-V monoclonal produced by an anti-human-annexin-V monoclonal antibody-producing hybridoma cell line clone HCA-627 of the accession number FERM BP-5284 deposited in the International Depositary Authority for the deposit of microorganism.

In the present invention, an annexin-V protein, i.e., annexin-V of an antigen protein can be derived in a purification manner from a tissue or a cell containing the annexin-V of an antigen protein present therein, and can be purified by removing connective tissues and lipids, for example, from heart tissues of a human dead body.

In the present invention, an anti-annexin-V monoclonal antibody can be obtained by fusing plasma cells and myeloma cells in a lymphocyte taken from a lymphatic organ of another animal species such as mouse immunized by annexin-V of an antigen protein, thereby forming hybridoma cells, and cultivating the formed hybridoma cells, for example, using an HAT culture medium.

Examples of the hybridoma cell lines produced by the anti-annexin-V monoclonal antibody in the present invention are two hybridoma cell lines: a hybridoma cell line of the accession number FERM BP-5284 which is disclosed in International Application (International Filing No. PCT/JP 95/02305 (International Laid-open No. WO96/15152)) and which was internationally deposited on Nov. 6, 1995 in the International Depositary Authority for the deposit of microorganism (Life Engineering Industrial Technology Research Institute belonging to Industrial Technology Board in Ministry of International Trade and Industry, 1–3, Higasi 1-Choume, Tsukuba-shi, Ibaragi-ken, Japan), and a hybridoma cell line of the accession number FERM BP-5286 likewise internationally deposited on Nov. 7, 1995 in the International Depositary Authority for the deposit of microorganism (Life Engineering Industrial Technology Research Institute belonging to Industrial Technology Board in Ministry of International Trade and Industry, 1–3, Higasi 1-Choume, Tsukuba-shi, Ibaragi-ken, Japan). The anti-annexin-V monoclonal antibody used in the present invention can be produced by selectively multiplying the hybridoma cell lines.

In the present invention, the anti-annexin-V monoclonal antibody can be produced by cultivating the hybridoma cell clone by a usual cultivating process, e.g., a high-density cultivating process or a spinner flask cultivating process, and purifying the cultivation supernatant by an affinity chromatography using a protein A-bound carrier or anti-mouse immunoglobulin-bound carrier.

As used in the present invention, the term "hybridoma cell line" means a hybridoma cell cultivated initially and thereafter, not to mention a cell-fused hybridoma cell.

An anti-annexin-V monoclonal antibody derived from an mammalian animal such as dog and having a specific reactivity to an antigen determinant side of an annexin-V antigen derived from an mammalian animal such as dog can be produced by administrating an annexin-V antigen derived from a mammalian animal such as dog for immunization of a mammalian animal, and fusing lymph cells and myeloma cells to provide a hybridoma cell line, by a process similar to a process for producing the anti-annexin-V monoclonal antibody derived from human. The anti-annexin-V monoclonal as used in the present invention means anti-annexin-V monoclonal antibodies derived from the mammalian animals, in addition to the above-described anti-annexin-V monoclonal antibody derived from human.

In the present invention, anti-human-annexin-V monoclonal antibodies fixed, for example, in a solid phase and used as primary antibodies in the measurement of a concentration of annexin-V in a human's urine by ELISA process, can be produced by cultivating the two hybridoma cell lines, e.g., the hybridoma cell line of the accession number FERM BP-5284 deposited internationally, and the hybridoma cell line of the accession number FERM BP-5286 likewise deposited internationally.

When one of the two anti-human-annexin-V monoclonal antibodies produced by the above-described hybridoma cell lines is used as a primary antibody in the measurement of the concentration of annexin-V in the human's urine by ELISA process, the other antibody can be labeled and used as a secondary antibody.

On example of a polyclonal antibody used as a labeled antibody, i.e., as a secondary antibody in the measurement of the concentration of annexin-V in the human's urine by ELISA process, is an anti-dog-32KP polyclonal antibody•Fab'-HRPO labeled antibody (which will be referred to as an anti-annexin-V polyclonal antibody HRPO labeled antibody hereinafter) disclosed in the above-described International Application (International Filing No.PCT/JP 95/02306 (International Laid-open No.WO96/15152).

According to the present invention, a urine is brought into an anti-annexin-V monoclonal antibody to perform the antigen/antibody reaction of annexin-V present in the urine with the anti-annexin-V monoclonal antibody, thereby forming an annexin-V antigen/anti-annexin-V monoclonal antibody complex, and the amount of the formed annexin-V antigen/anti-annexin-V monoclonal antibody complex is determined quantitatively. Therefore, annexin-V of a protein departing from cells can be measured easily by ELISA process by sampling an excreted urine, and the presence or absence of a disorder of an internal organ such as kidney, heart and lung, which is combined with disseminated intravascular coagulation syndrome or septicemia, not to mention a disorder of an internal organ such as stenocardia and myocardial infarction, can be easily diagnosed especially at an early stage. A variation in measurement of the annexin-V in the urine can be compared with a variation in measurement of annexin-V in blood for use in the diagnosis of acute nephritis.

EXAMPLES

In the following Examples, character M means a molar concentration, namely, molarity. In a solution of mixture, each M (molar concentration) means a molar concentration per liter of the solution.

Example 1

Process for Preparing Hybridoma (1) Purification of Human Annexin-V

The heart was excised from human adult cadaver or dead body, and the blood was removed therefrom. Then, the left ventricle was excised from the heart, and connective tissue and lipids were removed therefrom. These operations were carried out on ice or at a temperature of 4° C. A buffer solution of the following composition was added to the heart in an amount of ten parts by weight per part of the heart, i.e., in an amount as much as ten times the weight of the heart:

sucrose with a concentration of 250 mM;

ethylene glycol bis(2-aminoethyl ether) tetraacetate (EGTA) with a concentration of 0.5 mM;

phenylmethane sulfonyl fluoride (PMSF) with a concentration of 1 mM; and

Tris(tris(hydroxymethyl)aminomethane)HCL with a concentration of 10 mM and pH of 7.4, and the heart was homogenized by a homogenizer. The resulting homogenate was subjected to a centrifugal separation at 3000×g for 15 minutes. A solution of $CaCl_2$ with a concentration of 1 M was added to and mixed with the separated supernatant, so that the final concentration of the supernatant is of 2 mM. After the mixing, the mixture was subjected to a centrifugal separation at 28,000×g for 1 hour, and 2 ml of EDTA with a concentration of 10 mM was added to the sediment, whereby the sediment was suspended. The resulting sediment suspension was subjected to a centrifugal separation at 28,000×g for 1 hour.

The supernatant resulting from such centrifugal separation was subjected to a gel filtration column chromatography with Sephacryl S-300 (trade name) made by Pharmacia Co. for elution with pH 7.4 buffer solution B containing NaCl of 0.1 M and Tris-HCL of 30 mM. The fraction containing protein having a molecular weight of 35 dalton (Da) was recovered and passed through an anion-exchange column chromatography (Biogelagarose: trade name) with an eluent of 10 mM Tris-HCL solution (pH 7.4) containing NaCl with a concentration in a range of 0 to 0.3 M for purification by means of Nacl-concentration-gradient elution.

The human annexin-V purified in the above manner was subjected to a freeze-drying treatment and then dissolved by a 0.1 M buffer solution of sodium phosphate (pH of 7.6) and preserved at 4° C. The purity of the purified human annexin-V was measured by a polyacrylamide gel electrophoresis analysis (SDS-PAGE) to quantitatively determine a protein concentration.

To identify the antigen protein human annexin-V purified in the above manner, lysylendopeptidase was added thereto, and the resulting mixture was kept for 15 hours at a temperature of 37° C., thereby causing the lysylendopeptidase to react with the antigen protein human annexin-V to form a peptide. The peptide thus obtained was analyzed for an amino acid sequence by Edman method (see Edman P. "A method for the determination of the amino acid sequence in peptides", Arch. Biochem. Biophys., 1949, Vol.22, page 475) using PPSQ-10 Protein Sequencer made by Shimazu Corporation, whereby the amino acid sequences of two peptide moieties were determined.

One of the amino acid sequences of the two peptide moieties of the purified protein peptide is Glu-Tyr-Gly-Ser-Ser-Leu-Glu (SEQ ID NO: 1) from the N-terminal end, and the other amino acid sequence is Gly-Thr-Asp-Glu-Lys-Phe-Ile-Phe-Gly-Thr (SEQ ID No: 2) from the N-terminal end. Thus, the protein was identified as annexin-V.

(2) Immunization

100 μGram/0.5ml of the purified human annexin-V prepared in the above-described item (1) was mixed with the same amount of Freund's complete adjuvant to be emulsified. The emulsified human annexin-V was administrated as an antigen into the abdominal lumen of each of four female mice 5-weeks old in a dose such that the amount of the purified human annexin-V was in a range of 15–40 μg per one mouse. The administration was carried out at an interval of every two weeks for two months to immunize the mice. After the immunization, the antibody titer of each of the mice was measured for selection of mice having a higher antibody titer. After three weeks, 50 μg of the purified human annexin-V was further administrated to the selected mice through the tail vein for the final immunization.

(3) Cell Fusion

Three days later from the final immunization, the spleen was extracted from each of the BALB/c mice. The extracted spleen cells were suspended in EMEM culture medium to prepare a suspension of spleen cells. Then, the spleen cells were washed four times with EMEM culture medium (made by Nissui Co.) and then, the number of the cells was determined. The determined number of fresh spleen cells was of $7 \times 10^8$.

The cell fusion was carried out using, as a parent cell strain, a culture cell strain (P3-X63-Ag8•653 culture cells hereinafter reffer to as X63) resistant to 2-amino-6-oxy-8-azapuraine (8-azaguanine) and derived from BALB/c mouse myeloma.

The X63 cells in the logarithmic growth phase was employed to carry out the cultivation with an RPMI-1640 culture medium (containing 8-azaguanine at a concentration of 20 μg/ml) (made by GiBCO Co.) containing immobilized fetal calf serum (made by Intergen Co.) (which will be referred to as FCS hereinafter) at a concentration of 10%. From 3 day ago prior to the cell fusion, the cultivation was further carried out with RPMI-1640 culture medium containing 10% of FCS but free of 8-azaguanine. Even in this case, the cells in the logarithmic growth phase were used. The X63 cells were washed with the RPMI-1640 culture medium and then, the number of the cells was determined. The determined number of fresh X63 cells was $7 \times 10^7$.

Polyethylene glycol 4000 made by Shigma Co., was dissolved with the RPMI-1640 culture medium to give a concentration was 50% (W/V) and used in the cell fusion.

The spleen cells and the X63 cells were mixed together to give a ratio of the spleen cells:X63 cell=10:1, and then, the mixture was centrifuged at 1500 rpm for 5 minutes. The resulting supernatant was removed, and the cell pellet was disintegrated sufficiently and used in the cell fusion. The cell fusion was carried out using the polyethylene glycol prepared in the above-described manner and kept in temperature at 37° C. according to the method described in "Koller and Milsten: Nature, Vol.256, pages 495–497 (1975)" and "European Journal of Immunology, Vol.6, pages 511–519 (1976)".

The cell lines obtained after the cell fusion for the hybridoma formation was suspended in HAT selection culture medium comprising $1 \times 10^{-4}$ M hypoxanthine, $4 \times 10^{-7}$ M aminopterine and $1.6 \times 10^{-5}$ M thymidine contained in RPMI-1640 culture solution containing FCS of a 10% concentration added thereto, so as to give a spleen cell concentration of $2.0 \times 10^6$/ml. Then, the cell suspension was distributed in an amount of 50 µl into each of 96 wells in a micro test plate and then incubated in an atmosphere containing $CO_2$ in a concentration of 8% at a temperature of 37° C. and a humidity of 95% in a $CO_2$ sterile incubator.

(4) Screening

The HAT culture medium was added one drop by one drop to each U-bottomed well on the first day and the second day from the start of the incubation and further added two drops by two drops to each U-bottomed well on the seventh day and ninth day from the start of the incubation for the further incubation. Thereafter, the rearing was carried out in a culture medium free of HAT. Cell clones appeared ten days after the start of the incubation. After about ten to thirteen days from the start of the incubation, 50 µl of the incubation supernatant of the hybridoma cell line in each of the wells and 50 µl of the human annexin-V antigen solution (100 ng/ml) were placed into a U-shaped bottom of a micro-titer-plate, and 50 ml of a 20% suspension of Sepharose 4B having an anti-mouse immunoglobulin antibody combined thereto was further added to the U-shape bottom of the micro-titer-plate. The mixture was agitated for one hour at room temperature, and left to stand for 10 minutes after the agitation. Thereafter, it was observed that the anti-mouse immunoglobulin antibody-combined Sepharose 4B was completely sedimented on the well bottom. 50 µl Of the resulting supernatant was sampled, and a concentration of human-annexin-V antigen protein remaining in the supernatant was measured by the annexin-V ELISA method to provide the internationally-deposited hybridoma cell strain clones HCA-627 of the accession number FERM BP-5284 and the internationally-deposited hybridoma cell strain clones HDA-907 of the accession number FERM BP-5286.

It was confirmed that any of anti-annexin-V monoclonal antibodies produced from the internationally-deposited hybridoma cell strain clones HCA-627 of the accession number FERM BP-5284 and the internationally-deposited hybridoma cell strain clones HDA-907 of the accession number FERM BP-5286 has a specificity to the human annexin-V and the dog annexin-V.

(5) Analysis of Measuring Human Annexin-V (i) Preparation of Anti-human-annexin-V Monoclonal HRPO-labeled Antibody (A) Preparation of Anti-human-annexin-V Monoclonal Antibody F(ab')$_2$ In order to use, as a label, an IgG fraction of each of the internationally-deposited hybridoma cell strain clones HCA-627 of the accession number FERM BP-5284 and the internationally-deposited hybridoma cell strain clones HDA-907 of the accession number FERM BP-5286, 10 mg of each anti-human-annexin-V monoclonal antibody was concentrated by a centrifugal separation using a centrifugal separation-type concentrator (Centricon) 10 made by Amicon Co., so that 1 ml of the volume was obtained. Then, the concentrated antibody was dialyzed using a 0.1 M buffer solution of sodium acetate containing 0.2 M NaCl as a solvent.

A solution of pepsin (made by Sigma Co.) dissolved in a 0.1 M buffer solution (pH of 4.0) of sodium acetate containing 0.2 M NaCl was added to the dialyzed IgG solution, so that the pepsin was 4% of the amount of IgG, and the mixture was subjected to a reaction for 6 to 16 hours at a temperature of 37° C. After completion of the reaction, a fragment of an anti-human-annexin-V monoclonal F(ab') 2 was obtained by a molecular sieve chromatography using an equilibrium gel filtering Sephadex G-150 column (made by Pharmacia Co.) having a diameter of 1.6 cm and a length of 63 cm and equilibrated with a 0.1 M buffer solution of sodium borate (pH of 8.0).

(B) Preparation of Anti-human-annexin-V Monoclonal Fab'-SH

The fragment of the anti-human-annexin-V monoclonal antibody F(ab') 2 prepared in the item (A) of (5) in the Example 1 was further concentrated by centrifugal separation using the Centricon 10 which was the centrifugal separation-type concentrator, whereby a concentrated fraction of the fragment of the anti-human-annexin-V monoclonal antibody F(ab')$_2$ was prepared.

0.1 ml Of a 100 mM solution of 2-mercaptethyl amine hydrochloride (made by Kishida Chemicals Co.) was added to 1 ml of the concentrated fraction for reaction at 37° C. for 90 minutes. After completion of the reaction, the resulting material was subjected to a fractional purification using a equilibrium gel filtering Sephadex G-25 column having a diameter of 1.6 cm and a length of 20 cm and equilibrated with a buffer solution (pH of 6.0) of sodium phosphate containing 1 mM EDTA to provide an Fab'-SH fraction, which was then concentrated by centrifugal separation using the Centricon 10 which was the centrifugal separating concentrator, so that a ml of a volume was obtained. Thus, a concentrated fraction of the anti-human-annexin-V monoclonal antibody Fab'-SH produced from each of the clone HCA-627 and the clone HAD-907 was prepared.

(C) Preparation of HRPO Maleimide

On the other hand, 10 mg of HRPO (peroxidase of Wasabi-daikon (Japanese horse-radish) (made by Boehlinger Co.) was weighed as a protein content and dissolved in 1 ml of a 0.1 M buffer solution of sodium phosphate (pH 6.0). 100 µl Of a solution of N-hydroxysuccinimide ester (made by Zeeben Chemical Co.) dissolved in dimethylformamide (DMF) (made by Kisida Chemicals Co.), so that a final concentration of 25 mg/ml was obtained. The mixture was subjected to a reaction at 30° C. for 60 minutes to give maleimide ester of the HRPO. After the reaction, the solution was subjected to a centrifugal separation at 3,000 rpm for 5 minutes, and the resulting supernatant was subjected to a maleimide purification using the equilibrium gel filtering Sephadex G-25 column (made by pharmacia CO.) having a diameter of 1.6 cm and a length of 20 cm and equilibrated with a buffer solution (pH of 6.0) of sodium phosphate. This purified fraction of HRPO maleimide was further concentrated by centrifugal separation using the Centricon 10 which was the centrifugal separating concentrator, thus preparing a concentrated fraction of the HRPO maleimide.

(D) Preparation of Anti-human-annexin-V Monoclonal Fab'-HRPO Labeled Antibody

The concentrated fraction of the anti-human-annexin-V monoclonal antibody Fab'-SH produced in the item (B) of (5) in Example 1 and the HRPO maleimide fraction produced in the item (C) of (4) in Example 1 were mixed with each other to give a molar ratio of 1:1 for reaction at a temperature of 4° C. for 15 to 24 hours. After the reaction, 2-mercaptoethyl amine hydrochloride was added to the reaction solution to give a concentration of 2 mM in the reaction solution for reaction at a temperature of 37° C. for 20 minutes, thus blocking the unreacted HRPO maleimide. Then, the resulting solution was subjected to a molecular sieve chromatography using an Ultrogen ACA44 column (made by Pharmacia Co.) having a diameter of 1.6 cm and a length of 65 cm and equilibrated with a 20 mM buffer solution (pH of 5.6 of sodium phosphate-sodium citrate containing 0.15 M NaCl and 2.5 mM EDTA for removal of the unreacted anti-human-annexin-V monoclonal antibody Fab'-SH and HRPO maleimide to purify the anti-human-annexin-V monoclonal Fab'-SH labeled antibody (which will be referred to as an anti-human-annexin-V monoclonal HRPO labeled antibody hereinafter).

(ii) Preparation of HRPO Labeled Anti-dog-annexin-V Polyclonal Antibody (A) Preparation of Fraction of Anti-dog-polyclonal Antibody IgG Anti-dog-annexin-V polyclonal antiserum was produced by immunizing a rabbit with a purified annexin-V antigen derived from a dog myocardium. Added to 3 ml of this antiserum was an equal amount of phosphate-buffered physiological saline (PBS) and then, anhydrous sodium sulfate was added thereto with agitation to give a final concentration of 20%. Thereafter, the mixture was further agitated at room temperature for 1 hour. Then, the mixture was subjected to a centrifugal separation at 12,000 rpm for 10 minutes, and the sedimentation fraction was dissolved in about 3 ml of PBS. The resulting solution was dialyzed with a 20 mM buffer solution of sodium phosphate used as a solvent (pH 7.0). After completion of the dialysis, the dialyzed solution was subjected to an ion-exchange chromatography using a DEAE cellulose DE-52 column (made by Whatman Co.) having a diameter of 1.5 cm and a length of 6 cm and equilibrated with a 20 mM buffer solution of sodium phosphate (pH 7.0) for purification of an IgG fraction of the anti-dog-annexin-V polyclonal antibody. Thus, 13 mg of the purified IgG fraction was obtained from 3 ml of the anti-dog-annexin-V polyclonal antibody antiserum.

(B) Preparation of Anti-dog-annexin-V Polyclonal Antibody F(ab')$_2$

In order to use a purified IgG fraction of anti-dog-annexin-V polyclonal antibody for labeling, 12 mg of such antibody was subjected to a concentration using the Centricon 10 (made by Amicon Co.) which was the centrifugal separating concentrator to give a concentrated volume of 1 ml, followed by dialysis with a 0.1 M buffer solution of sodium acetate (pH of 4.5) containing 2M NaCl used as a solvent.

Added to the antibody solution resulting from the dialysis was pepsin (made by Sigma Co.) dissolved in a 0.1 M buffer solution of sodium acetate containing 0.2 M NaCl to give a concentration of 4% based on the IgG content, and the mixture was subjected to reaction at 37° C. for 16 hours. After the reaction, the reaction solution was subjected a molecular sieve chromatography using an equilibrium gel filtering Sephadex G-150 column (made by Pharmacia Co.) having a diameter of 1.6 cm and a length of 65 cm and equilibrated with a 0.1 M buffer solution of sodium borate (pH 8.0) for purification of an F(ab')$_2$ fraction of the antibody. The obtained fraction was dialyzed with a 0.1 M buffer solution (pH 6.0) of sodium phosphate containing 1 mM EDTA used as a solvent. After dialysis, the dialyzed solution was concentrated into a volume of 1 ml by centrifugal separation using the centrifugal separating concentrator, Centricon 10. The concentrated solution was used for preparation of a labeling antibody as anti-dog-annexin-V polyclonal antibody F(ab')$_2$. From the thus obtained IgG fraction of 12 mg of the anti-dog-annexin-V polyclonal antibody, about 7 mg of an F(ab')$_2$ fraction was prepared.

(C) Preparation of Anti-dog-annexin-V Polyclonal Fab'-SH

Added to a 7 mg/1 ml solution of the anti-dog-polyclonal ant-body F(ab')$_2$ fraction prepared by the method in the item (B) of (5–2) in Example 1, was 0.1 ml of a 100 mM solution of 2-mercaptoethyl amine hydrochloride (made by Kishida Chemicals Co.) for reaction at 37° C. for 90 minutes. After the reaction, the reaction solution was subjected to a chromatography using an equilibrium gel filtering Sephadex G-25 column (made by Pharmacia Co.) having a diameter of 1.6 cm and a length of 20 cm and equilibrated with a 0.1M buffer solution (pH 6.0) containing 1 mM EDTA for purification of an Fab'-SH fraction, followed by a concentration by centrifugal separation using the centrifugal separating concentrator 10 to give a concentrated volume of 1 ml, thereby purifying a concentrated fraction of anti-dog-annexin-V polyclonal antibody Fab'-SH. In this manner, 6.1 mg of the Fab'-SH concentrated fraction was obtained from 7 mg of the antibody F(ab')$_2$.

(D) Preparation of Anti-dog-annexin-V Polyclonal Fab'-HRPO Labeled Antibody

The anti-dog-annexin-V polyclonal antibody Fab'-SH fraction produced in the above manner and the HRPO maleimide fraction prepared in the item (C) of (5–1) in Example 1 were mixed together to give a molar ratio of 1:1, and the mixture was subjected to a reaction at a temperature of 4° C. for 15 to 24 hours. Thereafter, 2-mercaptoethyl amine hydrochloride was added to the reaction solution to give a concentration of 2 mM, and the mixture was subjected to a reaction at a temperature of 20° C. for 20 minutes, thereby blocking the unreacted HRPO maleimide. Then, the resulting material was subjected to a gel chromatography using the Ultrogel ACA44 column (made by Pharmaxia Co.) having a diameter of 1.6 cm and a length of 65 cm and equilibrated with a 20 mM buffer solution of sodium phosphate-sodium citrate containing 0.15 M NaCl and 2.5 mM EDTA for removal of the unreacted anti-dog-annexin-V polyclonal antibody Fab'-SH and HRPO maleimide to purify the anti-dog-annexin-V monoclonal Fab'-HRPO labeled antibody (which will be referred to as a dog-HRPO-labeled antibody hereinafter).

(iii) Measurement of Activity of HRPO

The measurement of the HRPO oxygen activity of each of the anti-human-annexin-V monoclonal HRPO-labeled antibody and the dog-HRPO-labeled antibody was carried out in the following manner: 20 μl Of the HRPO-labeled antibody was added to 2.98 ml of a 0.1 M buffer solution (pH 7.0) of sodium phosphate containing 0.2% phenol, 0.5 mM hydrogen peroxide and 0.15 mg/ml 4-aminoantipyrine to give a total volume of 3.0 ml, and the mixture was subjected to a reaction at a temperature of 37° C. for 5 minutes. The resulting reaction mixture was subjected to a measurement of absorbance at each of wavelengths of 492 nm and 692 nm by a two-wavelength photometric process according to Rate Assay. The HRPO activity could be determined by measuring a difference between the absorbances at the wavelengths of 492 nm and 692 nm per minute.

(iv) Solid-phase Preparation

Preparation of Anti-human-annexin-V Monoclonal Antibody Solid Phase

A monoclonal for use in a solid phase in a human-annexin-V measuring ELISA method was produced by purifying the IgG fraction of each of the clone HCA-627 and the clone HDA907. The IgG fraction of each of the human-annexin-V monoclonal antibodies was adjusted into a concentration of 30 µg/ml by use of a 0.1 M buffer solution of sodium phosphate (pH 7.5) containing 0.1% sodium azide, and distributed in an amount of 100 µl into each of wells of a micro-titer-plate (made Nunc Co.) for the ELISA method, for sensitization at 4° C. overnight. Then, each well of the micro-titer-plate was washed three times with a phosphate-buffered physiological saline buffer solution (PBS) containing a surfactant, Tween 20 at a concentration of 0.05% used as a washing liquid. Then, 300 µl of PBS (blocking solution) containing BSA at a concentration of 1% was supplied to each well for a further blocking at a temperature of 4° C. overnight. In this manner, an anti-human-annexin-V monoclonal antibody-sensitized antibody plate (which will be referred to as an anti-human-annexin-V monoclonal antibody plate hereinafter)

Example 2

The blocking solution of the anti-human-annexin-V monoclonal antibody solid-phase plate produced from the hybridoma cell line clone HAC-627 prepared as shown in the item (iv) of (5) in Example 1 was discarded. A 10 mM buffer solution of sodium phosphate (pH 7.0) containing BSA at a concentration of 1%, NaCl at a concentration of 0.15 M and EDTA at a concentration of 5 mM was supplied to each of wells. Thereafter, human-annexin-V antigen in the sampled urine was adjusted to give concentrations of 1.5625 ng/ml, 3.125 ng/ml, 6.25 ng/ml, 12.5 ng/ml, 25 ng/ml, 50 ng/ml and 100 ng/ml. A standard antigen solution was added in an mount of 20 µl to each of the wells and mixed for reaction at room temperature for 1 hour.

After the reaction, each of the wells was washed three times with a washing liquid. The above-described anti-human annexin-V monoclonal Fab'-HRPO labeled antibody produced at the above-described concentration from the clone HAD-907 was added in an amount of 100 µl to each of the wells and the mixture was subjected to a reaction at room temperature for 30 minutes. After the reaction, each of the wells was washed six times with a washing liquid. Then, 100 µl of an OPD substrate solution containing O-phenylenediamine at a concentration of 2 mg/ml and $H_2O_2$ at a concentration of 4 mM was added to a 0.1 M buffer solution of phosphate and citrate for reaction for 30 minutes. Thereafter, a 2 N solution of $H_2SO_4$ was added in an amount of 100 µl to each of the wells to terminate the reaction. The reaction mixture was subjected to a measurement of difference between absorbances by a two-wavelength photometric process using an ELISA plate reader at a primary wavelength of 592 nm and a secondary wavelength of 690 nm.

The difference between the absorbances, i.e., the differential absorbance determined by the two-wavelength process was determined by subtracting the absorbance at the secondary wavelength of 629 nm from the primary wavelength of 492 nm. A calibration curve showing the relationship between the concentration of the human-annexin-V antigen in the urine and the differential absorbance is shown in FIG. 1.

The calibration curve shown in FIG. 1 was made by plotting the differential absorbances determined by the two-wavelength process for every concentration of annexin-V in the standard solution of urine with respect to the concentration of human annexin-V standard antigen in the urine determined by the ELISA method using the anti-human-annexin-V monoclonal antibody produced from the clone HCA-627 and the anti-human-annexin-V monoclonal HRPO standard antibody produced from the clone HAD-907. The differential absorbance depends on the concentration of human annexin-V antigen in the urine and shows good values. The calibration curve is excellent one showing the absorbance which is risen depending on the concentration of human annexin-V in a substantially straight line up to the concentration of 100 ng/ml.

The concentration of annexin-V in the urine can be accurately read by using this calibration curve. As also apparent from FIG. 1, the concentration of annexin-V in the urine is satisfactorily reproducible even at a lower concentration value of 1 ng/ml, and such concentration can be measured, and the ELISA system is satisfactorily applicable to measure the concentration of annexin-V in the urine.

Example 3

The anti-human-annexin-V monoclonal antibody produced from the HCA-627 strain has a specificity to human annexin-V, dog annexin-V, rat annexin-V and bovine annexin-V.

In this example, the concentration of human annexin-V in the urine was measured by ELISA method using a combination of the anti-human-annexin-V monoclonal antibody and the anti-dog-annexin-V polyclonal antibody produced from the hybridoma cell line clone HCA-627 strain.

The anti-human-annexin-V monoclonal antibody produced from the hybridoma cell line HCA-627 was distributed in an amount of 100 µl at a concentration of 30 µg/ml into each of wells to form a solid phase well of the anti-human-annexin-V monoclonal antibody.

A reaction buffer solution having pH of 7.0 and containing a 10 mM buffer solution of sodium phosphate (pH of 7.5) having a concentration of 0.1 M, 0.15 M NaCl, 1% of BSA, 5 mM EDTA and 456 mg of gentamicin sulfate, was distributed in an amount of 100 µl into the solid phase well.

A standard solution was distributed in an amount of 20 µl into the solid phase well having the reaction buffer solution distributed thereto. The standard solution used in this example was a standard solution of human annexin-V antigen present in the sample urine.

After distribution of the standard solution, the mixture was agitated for one hour, whereby an antigen-antibody reaction was caused within each of the wells. When the antigen-antibody reaction time was lapsed, each of the wells was washed four times with a washing liquid. After the washing, 100 µl of a dog HRPO standard antibody (100 moo per ml of the reaction buffer solution) was added to each of the washed wells and agitated for 30 minutes to effect an antigen-antibody reaction. When the antigen-antibody reaction time was lapsed, each of the wells was washed eight times with a washing liquid. After the washing, an OPD substrate solution (containing 2 mg/ml of O-phenylene diamine and 4 mM $H_2O_2$ in a 0.1 M phosphate-citrate buffer solution) was added in an amount of 100 μl to each of the washed wells to effect a reaction for 30 minutes. Thereafter, a 2M solution of $H_2SO_4$ was added in an amount of 100 μl to each of the wells to terminate the coloring reaction, and a difference between the absorbances was measured at a primary wavelength of 492 and a secondary wavelength of 690 by the two-wavelength process by an ELISA plate reader.

Figure 2:
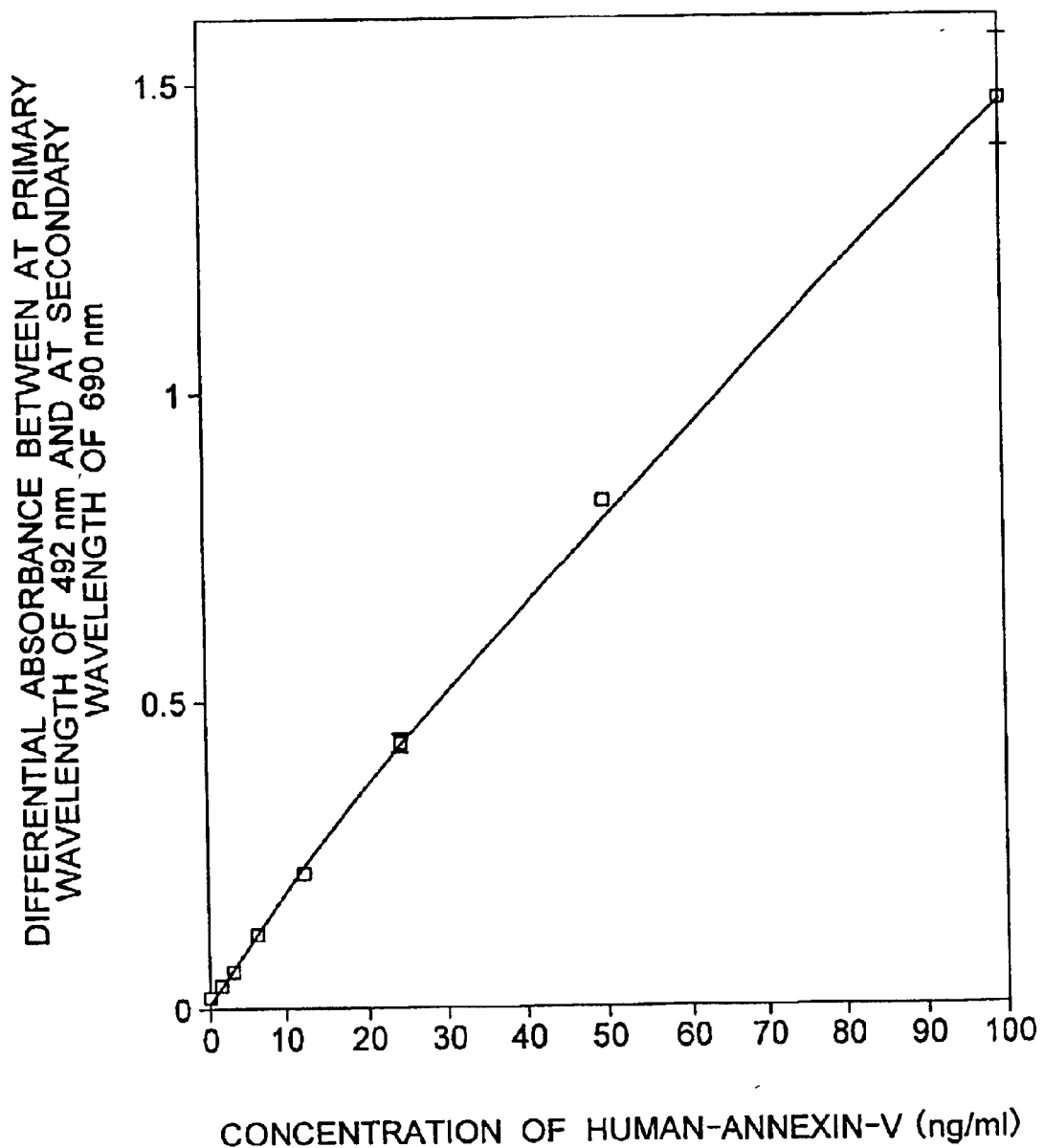
FIG. 2 is a calibration graph which is used in one embodiment for measuring a concentration of human annexin-V in a urine according to the present invention, and which is used in the measurement of a concentration of human annexin-V in a urine by ELISA process using a combination of an HRPO-labeled antibody derived from an anti-dog-annexin-V polyclonal antibody, and a solid phase anti-human-annexin-V monoclonal produced by an anti-human-annexin-V monoclonal antibody-producing hybridoma cell line clone HCA-627 of the accession number FERM BP-5284 deposited in the International Depositary Authority for the deposit of microorganism.

The differential absorbances determined by the two-wavelength process with respect to the concentration of the human annexin-V standard antigen in the urine measured by the ELISA method using the anti-human-annexin-V monoclonal antibody HCA-627 and the dog HRPO standard antibody were plotted for every concentration of annexin-V in the urine standard solution to make a calibration curve. The resulting calibration curve depends on the concentration of human annexin-V in the urine and shows good values. This calibration curve is shown in FIG. 2.

Example 4

In this example, the concentration of annexin-V in the urine was measured using a sampled urine in place of the standard solution used in Example 2. The differential absorbance was determined by subtracting the absorbance at a secondary wavelength of 690 nm from the absorbance at a primary wavelength of 492 nm. The concentration of annexin-V in a urine specimen was determined based on the calibration curve shown in FIG. 1

Used in this example was a titer-plate in which an anti-human-annexin-V monoclonal antibody derived from an supernatant resulting from the cultivation of the hybridoma cell line clone HCA-627 of reception No.FERM BP-5284 internationally cosigned was fixed in a solid phase. In this example, the measurement of the concentration of annexin-V in the urine was carried out by ELISA method using an anti-human-annexin-V monoclonal antibody derived from the clone HCA627 and an anti-human-annexin-V monoclonal antibody Gab'-HRPO labeled antibody derived from the clone HAD-907. The ELISA method was capable of measuring the concentration of annexin-V when the value of pH of the urine specimen was in a range of 5 to 8. When the concentration of annexin-V was to be measured, the pretreatment of the urine by adding a chelating agent such as EDTA for inhibiting the bonding of $Ca^{2+}$ was not required.

A blocking liquid in the anti-human-annexin-V monoclonal antibody solid phase plate was discarded, and a 10 mM buffer solution (pH of 7.0) of sodium phosphate containing 1% of BSA, 0.15 M NaCl and 5 mM EDTA was distributed into each of wells. Thereafter, the measurement of annexin-V in the sampled urine was carried out by distributing 20 μl of a sampled urine specimen into each of the wells in the titer-plate with the anti-human-annexin-V monoclonal antibody fixed in the solid phase.

After the distribution of the sampled urine specimen, the mixture was stirred at room temperature for one hour to effect an antigen-antibody reaction within each of the wells. After lapse of the antigen-antibody reaction time, each of the wells was washed three times with a washing liquid. The anti-human-annexin-V monoclonal antibody Gab'-HRPO labeled antibody derived from the clone HAD-907 and adjusted to a suitable concentration was added in an amount of 100 μl into each of the washed wells for reaction at room temperature for 30 minutes. After the reaction, each of the wells was washed six times with a washing liquid. Then, OPD substrate solution containing O-phenylene diamine at a concentration of 2 mg/ml and 4 nM $H_2O_2$ in 0.1 M buffer solution of phosphate-citrate was added in an amount of 100 μl to each of the wells for reaction for 30 minutes. Thereafter, 2N solution of $H_2SO_4$ was added in an amount of 100 μl to each of the wells to stop the coloring reaction, and a difference between absorbances was measured at a primary wavelength of 492 nm and a secondary wavelength of 690 by the two-wavelength process by the ELISA plate reader. The concentration of annexin-V in the urine specimen was determined using this differential absorbance on the basis of the calibration curve shown in FIG. 1.

Example 5

In this example, the concentration of annexin-V in the urine was measured using a sampled urine in place of the standard solution used in Example 3. The differential absorbance was determined by subtracting the absorbance at a secondary wavelength of 690 nm from the absorbance at a primary wavelength of 492 nm. The concentration of annexin-V in a urine specimen was determined based on the calibration curve shown in FIG. 1

Used in this example was a titer-plate in which an anti-human-annexin-V monoclonal antibody derived from an supernatant resulting from the cultivation of the hybridoma cell line clone HCA-627 of the accession number FERM BP-5284 internationally cosigned was fixed in a solid phase.

In this example, the measurement of the concentration of annexin-V in the urine was carried out by ELISA method using the anti-human-annexin-V monoclonal antibody HCA-627 and the dog HRPO labeled antibody. The ELISA method was capable of measuring the concentration of annexin-V when the value of pH of the urine specimen was in a range of 5 to 8. When the concentration of annexin-V was to be measured, the pretreatment of the urine by adding a chelating agent such as EDTA for inhibiting the bonding of $Ca^{2+}$ was not required.

A blocking liquid in the anti-human-annexin-V monoclonal antibody solid phase plate was discarded, and a 10 mM buffer solution (pH of 7.0) of sodium phosphate containing 1% of BSA, 0.15 M NaCl and 5 mM EDTA was distributed into each of wells. Thereafter, the measurement of annexin-V in the sampled urine was carried out by distributing 20 μl of a sampled urine specimen into each of the wells in the titer-plate with the anti-human-annexin-V monoclonal antibody fixed in the solid phase.

After the distribution of the sampled urine specimen, the mixture was stirred at room temperature for one hour to effect an antigen-antibody reaction within each of the wells. After lapse of the antigen-antibody reaction time, each of the wells was washed four times with a washing liquid. The dog HRPO labeled antibody (100 mU per ml of the reaction buffer solution) was added in an amount of 100 μl into each of the washed wells and stirred at room temperature for 30 minutes to effect an antigen-antibody reaction. After lapse of the antigen-antibody reaction time, each of the wells was washed eight times with a washing liquid. After the washing, an OPD substrate solution was added in an amount of 100 μl to each of the washed wells for coloring reaction at room temperature for 30 minutes. For the obtained color, absorbances at a primary wavelength of 492 nm and a secondary wavelength of 690 were measured, and a differential absorbance was determined by subtracting the absorbance at the secondary wavelength of 690 nm from the absorbances at the primary wavelength of 492nm. In this manner, the concentration of annexin-V was determined on the basis of the calibration curve shown in FIG. 2.

Example 6

The measurement of the concentration of annexin-V in a sampled urine was carried out in the method described in Example 4. After lapse of the coloring reaction time, a reaction stopping solution (2 N solution of $H_2O_4$) was added in an amount of 100 $\mu l$ to each of the wells to stop the coloring reaction, and an absorbance was measured at a primary wavelength of 492 nm and a secondary wavelength of 690 nm by the ELISA plate reader. In this manner, the concentration of annexin-V of the antigen protein in the urine specimen was determined on the basis of the calibration curve shown in FIG. 1.

In this example, a men fifty two years old was subjected to an aorta replacing operation five years ago. He was in fever continuously two weeks, and there was a suspicion of an infectious endocarditis for him.

In order to measure the concentration of annexin-V in his urine, the urine was immediately sampled from him. The urine sampled on a first day was represented by a urine specimen 1. Then, urine was sampled from him on second, third, fourth, sixth and eighth days and represented by second, third, fourth, sixth and eighth specimens, respectively. For every urine specimens, the concentration of annexin-V in the urine was determined on the sampling day by the analysis of annexin-V in the urine described in Example 4. The concentrations of annexin-V in the urine specimens are as given in Table 1.

TABLE 1

| Sampling day | Concentration of annexin-V in urine specimen (ng/ml) |
| --- | --- |
| First day | 1.2 |
| Second day | 10.6 |
| Third day | 16.0 |
| Fourth day | 14.6 |
| Sixth day | 17.0 |
| Eighth day | 7.9 |

With regard to the concentration of annexin-V in the urine, the concentration of annexin-V in the urine specimen sampled on the first day was 1.2 ng/ml which was in a normal range, but the concentration of annexin-V in the urine specimen was increased to 10.6 ng/ml on the second day higher than that on the first day. After the second day, the concentration of annexin-V in the urine was increased, and an increased in concentration of annexin-V in the blood was also observed. Thus, he was diagnosed as having a complication of an internal organ disorder.

The number of platelets was 38,000 on the second day and was decreased to 29,000 on the third day, a decrease in FDP was observed. Thus, he was diagnosed as being DIC. The concentration of annexin-V on the second day was 10.6 ng/ml, and he was diagnosed as having a complication of an internal organ disorder. On the third day, increases in urea nitrogen and creatinine were observed and thus, the complication of an internal organ disorder was made clear. The blood transfusion of platelets and the administration of an antibiotic substance into the patient were started, whereby the patient was cured to such an extent that the whole body state was improved; the appetite was recovered; and he could walk around the bed.

This disease case was an example that the presence of the internal organ disorder could be diagnosed at an early stage by the measurement of the concentration of annexin-V in the urine.

The examination of the concentration of annexin-V in the urine for 20 normal healthy persons, more specifically, for 10 men and 10 women in an age range of 22 to 65 showed that the concentration of annexin-V in the urine was 2.3 ng/ml at the maximum; 0.3 ng/ml at the minimum; and 1.6 mg/ml at the average.

Example 7

In this embodiment, the measurement of the concentration of annexin-V in a rat's urine was carried out in the same manner as in Example 5. The differential absorbance was determined by subtracting the absorbance at the secondary wavelength of 690 from the absorbance at the primary wavelength of 492, and the concentration of annexin-V in the urine specimen was determined on the basis of the calibration curve shown in FIG. 2.

A given amount of annexin-V was injected into a vein, and the concentration of annexin-V appearing in a urine was measured. It has been found in this experiment that if the concentration of annexin-V in blood is increased, the concentration of annexin-V in the urine is increased.

More specifically, 5 $\mu g$ of annexin-V (recombinant annexin-V) was injected into the femoral vein of a rat having a weight of 350 g, and the concentration of annexin-V in the urine was measured with the passage of time. Results are given in Table 2 below.

TABLE 2

| | Immediately after injection | 15 minutes later | 30 minutes later | 60 minutes later | 120 minutes later |
| --- | --- | --- | --- | --- | --- |
| Experiment example | 1.0 | 12.4 | 48.2 | 74.5 | 15.2 |

(Unit: ng/ml)

Recovery Test

The test of recovery of annexin-V was carried out for three examples. Test results are given in Table 3 below. When annexin-V protein was added in amounts of 12.5 ng/ml and 25.0 ng/ml to a urine having an annexin-V value in a range of 1.8 to 2.9 ng/ml, the rate of annexin-V recovered from the urine in a separating manner by the antigen-antibody reaction assumed 92.8 to 99.2% in each case, which was an extremely good result.

TABLE 3

| Type of sample | Examination No. | A Measured concentration of annexin-V in urine specimen (ng/ml) | B Measured concentration of annexin-V added (ng/ml) | C amount of human annexin-V antigen recovered (ng/ml) | Rate of human annexin-V recovered (%) |
| --- | --- | --- | --- | --- | --- |
| Urine | N-1 | 2.5 | 12.5 | 14.9 | 99.2 |
| | | | 25.0 | 26.6 | 96.4 |
| Urine | N-2 | 1.8 | 12.5 | 13.4 | 92.8 |
| | | | 25.0 | 25.2 | 93.6 |
| Urine | N-3 | 2.9 | 12.5 | 14.9 | 96.0 |
| | | | 25.0 | 26.9 | 96.0 |

Recovery rate = [(C − A)/B] × 100

The test of influence of pH in the measurement of the concentration of annexin-V in a urine was carried out in the following manner: The pH value in the urine was adjusted to 4 to 8 by adding a suitable amount of 1 N solution of hydrochloric acid and a suitable amount of 1 N solution of sodium hydroxide into the urine, and a concentration of annexin-V was measured. Results are given in Table 4 below. *Mark in Table 4 represents a value of concentration of annexin-V in the urine in example itself.

TABLE 4

|  | pH 4 | pH 5 | pH 6 | pH 7 | pH 8 |
|---|---|---|---|---|---|
| Case example 1 | 2.5 | 8.3 | 8.6 * | 8.7 | 9.1 |
| Case example 2 | 1.2 | 3.9 | 3.8 * | 3.8 | 3.9 |
| Case example 3 | 0.3 | 2.0 | 2.1 * | 2.1 | 2.2 |

(Unit: ng/ml)

This example shows that the measurement of concentration of annexin-V in the urine according to the present invention can be performed in a range of pH value of 5 to 8.

Example 8

Acute nephritis was experimentally developed in a rat, and a concentration of annexin-V in a rat's urine was measured by a sandwich ELISA method using an anti-annexin-V monoclonal antibody and an anti-annexin-V polyclonal antibody.

The experimental acute nephritis was developed in the following manner: the fundus membrane of glomerulus was separated from the renal tapetum of a bovine and subjected to a solubilizing treatment. The resulting material was subjected to a gel filtration column chromatography to provide an eluted fraction of a nephritis causing antigen. The eluted fraction was mixed in an amount of 30 µg with an equal amount of Freudian complete adjuvant, and the resulting mixture was intradermally injected into a foot sole of a single rat (Wistar-Kyoto type rat) to develop an acute nephritis similar to that of a human.

In order to measure a concentration of annexin-V in a urine, the urine was sampled one week later after the intradermal injection and named urine specimen 1 after one week. Then, the urine was sampled two, three, four and five weeks later and named urine specimens after two, three, four and five weeks. For every urine specimen, the concentration of annexin-V in the urine was measured on the sampling day by the analysis of annexin-V in the urine described in the above-described Example 4. The concentrations of annexin-V in the urine specimens are as given in Table 5 below.

TABLE 5

| Sampling day after intradermal injection on sampling day | Concentration of annexin-V in urine specimen (ng/ml) | Amount on protein in urine specimen (mg/ml) |
|---|---|---|
| one week later | 0.8 | 0.3 |
| two weeks later | 23.2 | 15.4 |
| three weeks later | 52.6 | 29.9 |
| four weeks later | 33.6 | 52.4 |
| five weeks later | 17.9 | 33.6 |

As given in Table 5, the concentration of annexin-V in the urine was suddenly increased till the third week and showed a maximum value in the third week prior to the amount of the protein in the urine. The measurement of the concentration of annexin-V in the urine is affective for the diagnosis of the experimetal acute nephritis.

An increase in concentration of annexin-V in blood was not observed every week later. The behavior of the concentration of annexin-V in the blood and in the urine is considered as being one of characteristics of the acute nephritis.

Example 9

This example relates to a patient who is 20 years old men diagnosed as suffering from a nephrotic syndrome. The patient complained of a languor. The examination showed an edema on the whole body and the albuminuria of 12.7 g/day and thus, the patient was diagnosed as suffering from a nephrotic syndrome. The concentration of annexin-V in the patient's urine and the amount of protein in the urine were measured. In this case, the concentration of annexin-V in the patient's urine was measured by the analysis of annexin-V in the urine described in the above-described Example 4. The results of the measurement are as given in Table 6 below.

TABLE 6

| Day of remedy | Concentration of annexin-V in urine (ng/ml) | Amount of protein in urine (g/day) |
|---|---|---|
| First day | 63.7 | 12.7 |
| Second day | 69.5 | 15.8 |
| Third day | 42.8 | 19.3 |
| Sixth day | 33.2 | 13.4 |
| Eleventh day | 24.5 | 8.3 |
| Twentieth day | 13.4 | 7.5 |

As can be seen from above Table, on the first day of remedy, the concentration of annexin-V in the patient's urine was as high as 63.7 ng/ml, and the amount of protein in the patient's urine per day was also as high as 12.7 g/day. However, on the twentieth day of remedy, the concentration of annexin-V in the patient's urine showed a remarkably decreased value of 13.4 ng/ml, and the amount of protein in the patient's urine per day also showed a remarkably decreased value of 7.5 g/day. Thus, the edema on the whole body of the patient was eliminated, and in this way, an improvement by a remedy effect was observed.

It was found that the measured concentration value of annexin-V in the urine corresponds to a variation in amount of protein in the urine, and the diagnosis of the nephrotic syndrome and the recuperation of the nephrotic syndrome by the remedy can be examined by the concentration of annexin-V in the urine or by both of the concentration of annexin-V and the amount of protein per day in the urine. As can be seen in this example, the concentration of annexin-V in the urine is useful for examining the diagnosis of the nephrotic syndrome and the recuperation of the nephrotic syndrome by the remedy.

Industrial Applicability

According to the present invention, a urine is brought into contact with an anti-annexin-V monoclonal antibody, whereby annexin-V in the urine is subjected to an antigen-antibody reaction with the anti-annexin-V monoclonal antibody to form an annexin-V antigen/anti-annexin-V monoclonal antibody complex. The formed annexin-V antigen/anti-annexin-V monoclonal antibody complex is quantitatively analyzed. Therefore, annexin-V of a protein departing from the cell and excreted into the urine can be easily measured from the sampled urine by ELISA method.

Moreover, the present invention is applicable to the diagnosis of the presence and absence of a disease of an internal organ such as kidney, heart and lung, which is combined with, for example, disseminated intravascular coagulation syndrome or septicemia, and particularly, the present invention enables the disease of such internal organ to be diagnosed easily at the early state. Therefore, the present invention is useful for the development of the remedy method, the remedy and diagnosis medicines and the diagnosis method for the internal organ such as kidney, heart and lung, which is combined with disseminated intravascular coagulation syndrome or septicemia, and for a means for providing results of a clinical demonstration.

first anti-annexin-V monoclonal antibody to form an antibody complex, bonding a labeled anti-annexin-V polyclonal antibody or a second labeled anti-annexin-V monoclonal antibody to the annexin-V antigen of said formed antibody complex to form an amount of a bonded product of annexin-V antigen/antibody complex/anti-annexin-V polyclonal antibody or second anti-annexin-V monoclonal antibody, an quantitatively measuring the amount of said bounded product.

3. The process for diagnosing acute nephritis by use of urine according to claim 2, wherein said first anti-annexin-V

What is claimed is:

1. A process for diagnosing acute nephritis in a patient by use of urine, comprising the steps of:

(A) measuring concentrations of annexin-V in samples of urine excreted by the patient at two different time points;

(B) determining a difference between measured values of concentrations of annexin-V in the samples of urine at said two different time points;

(C) measuring concentrations of annexin-V in samples of blood of said patient at said two different time points;

(D) determining a difference between measured values of concentrations of annexin-V in the samples of blood at said two different time points;

(E) comparing said difference between measured values of concentrations of annexin-V in the samples of urine with said difference between measured values of concentrations of annexin-V in the samples of blood; and (F) diagnosing acute nephritis based on an increasing concentration of annexin-V in the urine but not in the blood of the patient.

2. The process for diagnosing acute nephritis by use of urine according to claim 1, wherein the concentration of annexin-V in the urine is measured by subjecting annexin-V antigen in the urine to an antigen-antibody reaction with a monoclonal antibody is produced by a hybridoma cell line deposited under the number FERM BP-5284 or FERM BP-5286, and said second anti-annexin-V monoclonal labeled antibody is formed from a product produced by the hybridoma cell line deposited under the number FERM BP-5284 or FERM PB-5286, wherein said first anti-annexin-V monoclonal antibody and the second anti-annexin-V monoclonal antibody forming said second anti-annexin-V monoclonal labeled antibody are different from each other.

4. A process for diagnosing acute nephritis in a patient by use of urine, comprising the steps of:

(A) bringing samples of urine taken from the patient at two different time points into contact with an anti-annexin-V monoclonal antibody to perform an antigen/antibody reaction of annexin-V antigen in each of the urine samples with said anti-annexin-V monoclonal antibody, thereby forming an amount of an annexin-V antigen/anti-annexin-V monoclonal antibody complex;

(B) quantitatively measuring the amount of said formed annexin-V antigen/anti-annexin-V monoclonal antibody complex in step (A), thereby determining a concentration of annexin-V in each of the urine samples and determining a difference between the concentrations of annexin-V in the urine samples taken at said two different time points (C) bringing annexin-V present in a sample of blood taken from the patient at said two different time points into contact with an anti-annexin-V monoclonal antibody to perform an antigen/antibody reaction of annexin-V antigen in each of the blood samples with said anti-annexin-V monoclonal antibody, thereby forming an amount of an annexin-V antigen/anti-annexin-V monoclonal antibody complex;

(D) quantitatively measuring the amount of said formed annexin-V antigen/anti-annexin-V monoclonal antibody complex in step (C), thereby determining a concentration of annexin-V in each of the blood samples and determining a difference between the concentrations of annexin-V in the blood samples taken at said two diffrent time points;

(E) comparing the difference between the annexin-V concentrations in the urine samples and the difference between the annexin-V concentrations in the blood samples taken at said two different time points with each other; and (F) diagnosing acute nephritis based on an increasing concentration of annexin-V in the urine but not in the blood of the patient.

5. The process for diagnosing acute nephritis by use of urine according to claim 4, wherein said anti-annexin-V monoclonal antibody is produced by a hybridoma cell line deposited under the number FERM BP-5284 or a hybridoma cell line deposited under the number FERM BP-5286.

* * * * *

SEQUENCE LISTING

```
<160> NUMBER OF SEQ ID NOS: 2

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu Tyr Gly Ser Ser Leu Glu
 1               5

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Thr Asp Glu Glu Lys Phe Ile Thr Ile Phe Gly Thr
 1               5                  10
```